(12) United States Patent
Moon et al.

(10) Patent No.: US 8,053,575 B2
(45) Date of Patent: Nov. 8, 2011

(54) NITROGEN-CONTAINING HETEROAROMATIC LIGAND-TRANSITION METAL COMPLEXES, BUFFER LAYER COMPRISING THE COMPLEXES AND ORGANIC THIN FILM TRANSISTOR COMPRISING THE BUFFER LAYER

(75) Inventors: Hyun Sik Moon, Seoul (KR); Do Hwan Kim, Seoul (KR); Jong Jin Park, Yongin-si (KR); Jung Seok Hahn, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 848 days.

(21) Appl. No.: 11/980,349

(22) Filed: Oct. 31, 2007

(65) Prior Publication Data
US 2008/0197346 A1    Aug. 21, 2008

(30) Foreign Application Priority Data

Feb. 16, 2007   (KR) ........................ 10-2007-0016551

(51) Int. Cl.
*C07F 15/00* (2006.01)
*H01L 51/50* (2006.01)
(52) U.S. Cl. ........................... 546/10; 313/504; 428/690
(58) Field of Classification Search .................... 546/10; 313/504; 428/690
See application file for complete search history.

(56) References Cited

U.S. PATENT DOCUMENTS
7,282,586 B1 * 10/2007 Yen et al. ....................... 546/88
* cited by examiner

*Primary Examiner* — Charanjit Aulakh
(74) *Attorney, Agent, or Firm* — Harness, Dickey & Pierce, P.L.C.

(57) ABSTRACT

Example embodiments provide a nitrogen-containing heteroaromatic ligand-transition metal complex, a buffer layer including the complex, which may improve the injection and transport of electrical charges, an organic thin film transistor and an electronic device including the buffer layer, in which the injection of electrons or holes and the transport of charges between layers are accelerated, thereby improving the efficiency thereof, and methods of manufacturing the same.

11 Claims, 3 Drawing Sheets

NITROGEN-CONTAINING HETEROAROMATIC LIGAND-TRANSITION METAL COMPLEXES, BUFFER LAYER COMPRISING THE COMPLEXES AND ORGANIC THIN FILM TRANSISTOR COMPRISING THE BUFFER LAYER

PRIORITY STATEMENT

This application claims priority under U.S.C. §119 to Korean Patent Application No. 10-2007-0016551, filed on Feb. 16, 2007, in the Korean Intellectual Property Office (KIPO), the entire contents of which are incorporated herein by reference.

BACKGROUND

1. Field

Example embodiments relate to a nitrogen-containing heteroaromatic ligand-transition metal complex, a buffer layer comprising the complex, an organic thin film transistor and an electronic device comprising the buffer layer and methods of manufacturing the same. Other example embodiments relate to a heteroaromatic ligand-transition metal complex containing nitrogen, a buffer layer comprising the complex, which may improve the injection and transport of electrical charges, an organic thin film transistor and an electronic device comprising the buffer layer and methods of manufacturing the same.

2. Description of the Related Art

Organic material-based device technologies may complement the field of silicon-based electronic devices in the field of large area flexible displays. Organic Thin Film Transistor (OTFT) technologies, which are being researched, may be sufficiently competitive by not requiring integration and providing improved performance, compared to silicon-based Thin Film Transistors (TFTs).

The infrastructure cost of OTFTs may be only about ⅓ of that of amorphous silicon TFTs, and OTFTs may be more easily operated than an inorganic substrate and may be continuously processed. Therefore, the cost of processing OTFTs may be reduced compared to conventional TFTs. In order to apply the OTFTs to the backplane of a display, the characteristics of OTFTs may be improved through the design and synthesis of organic semiconductors, the design of devices and the development of process technologies.

The characteristics of TFTs may be determined by the injection and transport of electrons and holes. Electrons and holes may be injected into a channel layer without causing contact resistance between electrodes and a semiconductor layer, and then the electrons and holes may be more rapidly transported from the channel layer. Unlike silicon TFTs, in which ohmic contact more easily occurs, the characteristics of OTFTs may be mainly deteriorated by contact resistance. When metals come into contact with a semiconductor layer or an electrical charge transfer layer having a relatively low concentration of impurities, a potential barrier may be formed at the contact surface therebetween, thereby increasing resistance. The height of the potential barrier may depend on the difference between energy levels of electrodes and a semiconductor layer or an electrical charge transfer layer, and the state of the connection therebetween.

Conventional methods of surface-treating electrodes, which are used to reduce contact resistance between electrodes and a semiconductor layer or an electrical charge transfer layer, may include methods of using a Self-Assembled Monolayer (SAM) and/or methods of using a buffer layer. Among the methods, the method of using a buffer layer may dispose a layer containing a material for reducing contact resistance between electrodes and a semiconductor layer or an electrical charge transfer layer, and may be mainly applied to a process of producing an organic thin film transistor (OTFT) and/or an organic light emitting diode (OELD).

Low-molecular-weight semiconductors, which may form a film in a vacuum process, e.g., triphenyl amine derivatives and/or acid-doped conductive polymers, which may form a film in a solution process, e.g., poly(3,4-ethylenedioxythiophene) and/or poly(styrenesulfonate), have been used as the buffer layer materials.

Buffer layer materials, which may form a film in a solution process, may be required in order to reduce costs. However, when acid-doped conductive polymers are used as the buffer layer materials, an acid dopant may be diffused to a channel layer, thereby decreasing the stability of devices.

SUMMARY

Accordingly, example embodiments have been made to develop buffer layer materials, which may form a film in a solution process without use of an acid dopant. Example embodiments provide a heteroaromatic ligand-transition metal complex containing nitrogen. Example embodiments also provide a buffer layer including the complex, which may improve the injection and transport of electrical charges. Example embodiments also provide an organic thin film transistor and an electronic device including the buffer layer and methods of manufacturing the same.

BRIEF DESCRIPTION OF THE DRAWINGS

Example embodiments will be more clearly understood from the following detailed description taken in conjunction with the accompanying drawings. FIGS. 1-6 represent non-limiting, example embodiments as described herein.

FIGS. 1 and 2 are schematic sectional views illustrating the bottom contact type OTFTs, respectively, according to example embodiments;

FIG. 3 is a graph showing a UV-visible spectrum of Flu-SPNB-Flu-Au synthesized in Preparation Examples 1 to 4 according to example embodiments;

FIG. 4 is a schematic sectional view showing a test device manufactured in Example 1 according to example embodiments; and FIG. 5 is a graph showing current-voltage characteristic curves according to Example 1 and Comparative Example 1 of example embodiments.

Figure 1:
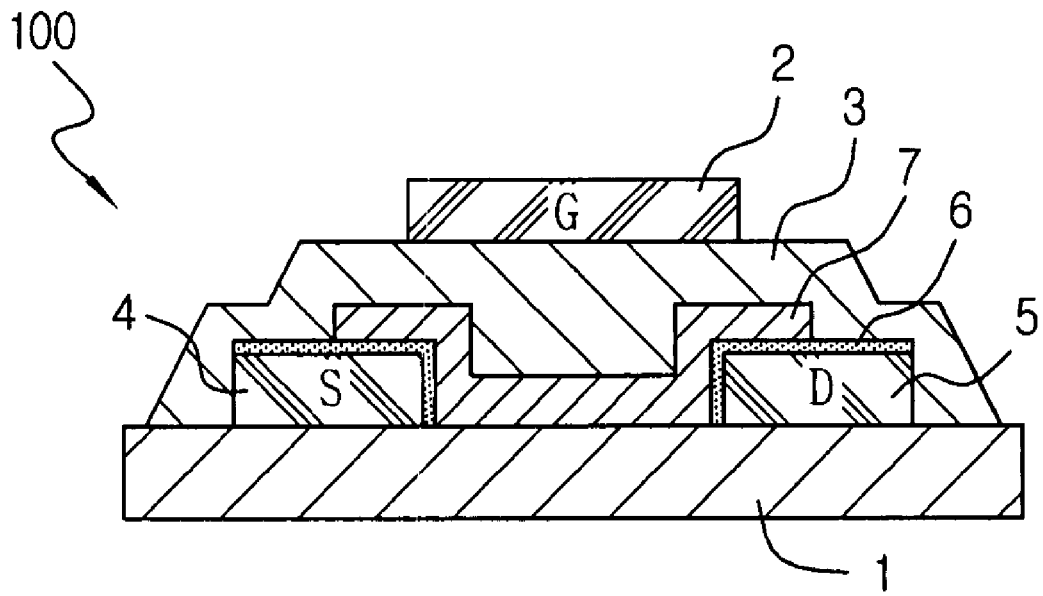

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Hereinafter, example embodiments will be described in detail with reference to the attached drawings. Reference now should be made to the drawings, in which the same reference numerals are used throughout the different drawings to designate the same or similar components. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments provide a nitrogen-containing heteroaromatic ligand-transition metal complex, represented by the following formula:

$$[R_1-X-R_2] \cdot [M(Y)_m]^- \qquad \text{Formula (1)}$$

wherein,

X is a substituted or unsubstituted nitrogen-containing heteroaromatic organic group of about 2 to about 30 carbon atoms, each of $R_1$ and $R_2$ is independently selected from the group consisting of a substituted or unsubstituted alkyl group of about 1 to about 30 carbon atoms; a substituted or unsubstituted hetero alkyl group of about 1 to about 30 carbon atoms; a substituted or unsubstituted alkoxy group of about 1 to about 30 carbon atoms; a substituted or unsubstituted hetero alkoxy group of about 1 to about 30 carbon atoms; a substituted or unsubstituted aryl group of about 6 to about 30 carbon atoms; a substituted or unsubstituted arylalkyl group of about 6 to about 30 carbon atoms; a substituted or unsubstituted aryloxy group of about 6 to about 30 carbon atoms; a substituted or unsubstituted hetero aryl group of about 2 to about 30 carbon atoms; a substituted or unsubstituted hetero arylalkyl group of about 2 to about 30 carbon atoms; a substituted or unsubstituted hetero aryloxy group of about 2 to about 30 carbon atoms; a substituted or unsubstituted cycloalkyl group of about 5 to about 20 carbon atoms; a hetero substituted or unsubstituted cycloalkyl group of about 2 to about 30 carbon atoms; a substituted or unsubstituted alkylester group of about 1 to about 30 carbon atoms; a substituted or unsubstituted hetero alkylester group of about 1 to about 30 carbon atoms; a substituted or unsubstituted aryl ester group of about 6 to about 30 carbon atoms; and a substituted or unsubstituted hetero aryl ester group of about 2 to about 30 carbon atoms, M is a transition metal atom selected from the group consisting of gold (Au), copper (Cu), palladium (Pd) and platinum (Pt), Y is selected from the group consisting of a halide, a hydroxyl group, and an acetate functional group (OAc), and m is an integer of about 3 to about 4.

In the above Formula (1), X may be selected from the group consisting of the heteroaromatic organic groups represented by the following Formula (2):

Formula (2)

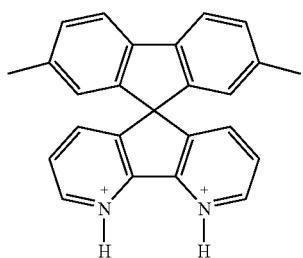

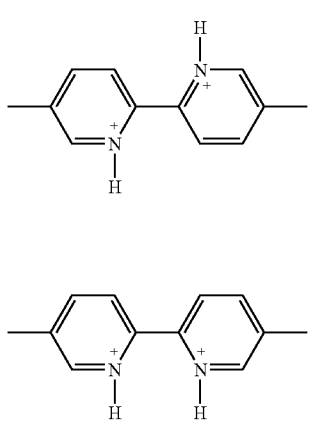

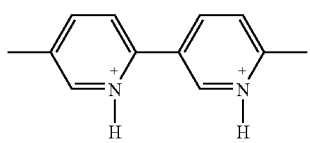

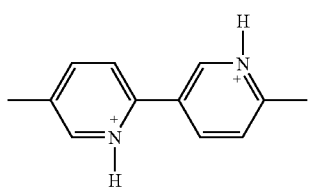

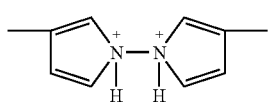

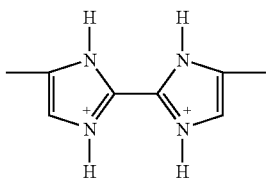

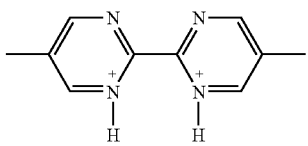

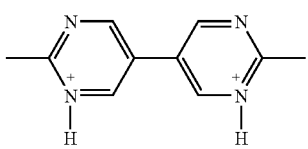

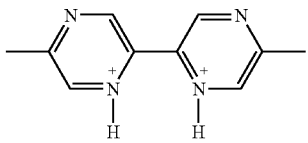

Further, in the above Formula (1), each of $R_1$ and $R_2$ may be independently a substituted or unsubstituted aryl group of about 6 to about 30 carbon atoms, or a substituted or unsubstituted hetero aryl group of about 2 to about 30 carbon atoms.

The substitution group, with which the aryl group or hetero aryl group is substituted, may be one or more selected from the group consisting of a linear or branched alkyl group of about 1 to about 10 carbon atoms, a perfluoroalkyl group, a halogen atom, a hydroxy group, a nitro group, an amino group, a cyano group, an alkoxy group, an amidino group and a carboxyl group.

The nitrogen-containing heteroaromatic ligand-transition metal complex may be represented by the following Formula (3):

Formula (3)

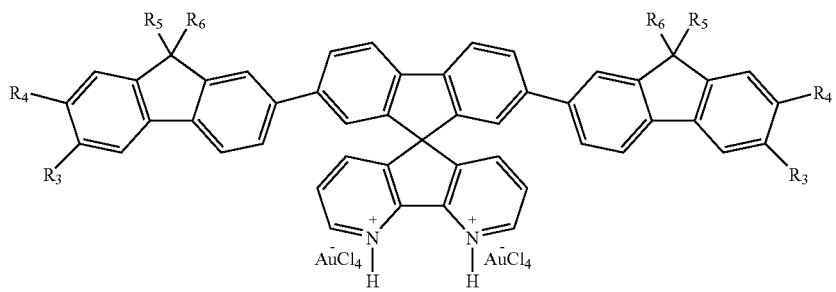

wherein each of $R_3$ to $R_6$ is independently selected from the group consisting of a linear or branched alkyl group of about 1 to about 10 carbon atoms, a perfluoroalkyl group, a hydrogen atom, a halogen atom, a hydroxy group, a nitro group, an amino group, a cyano group, an alkoxy group, an amidino group and a carboxyl group. At least one R may be a linear or branched alkyl group of about 1 to about 10 carbon atoms and/or a perfluoroalkyl group.

For example, the nitrogen-containing heteroaromatic ligand-transition metal complex may be represented by the following Formulas (4) to (6):

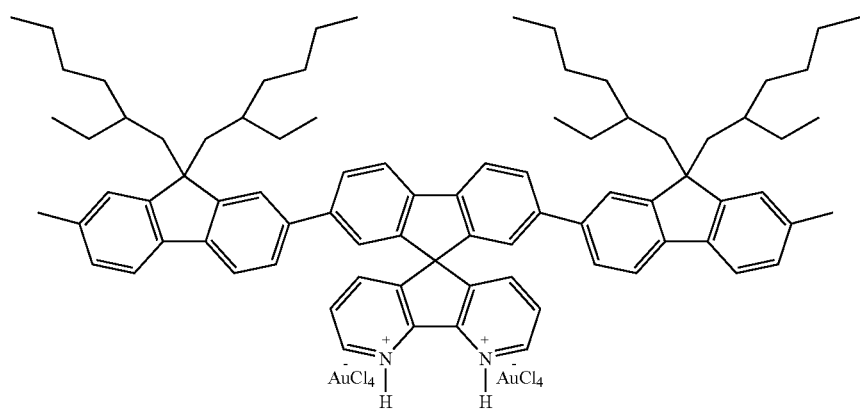

Formula (4)

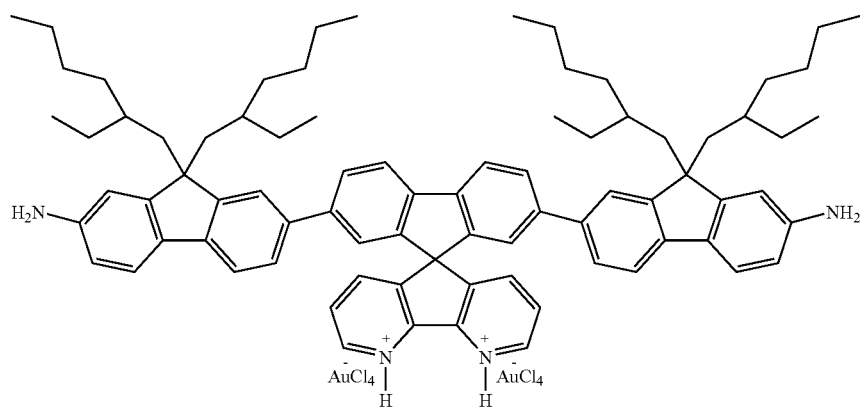

Formula (5)

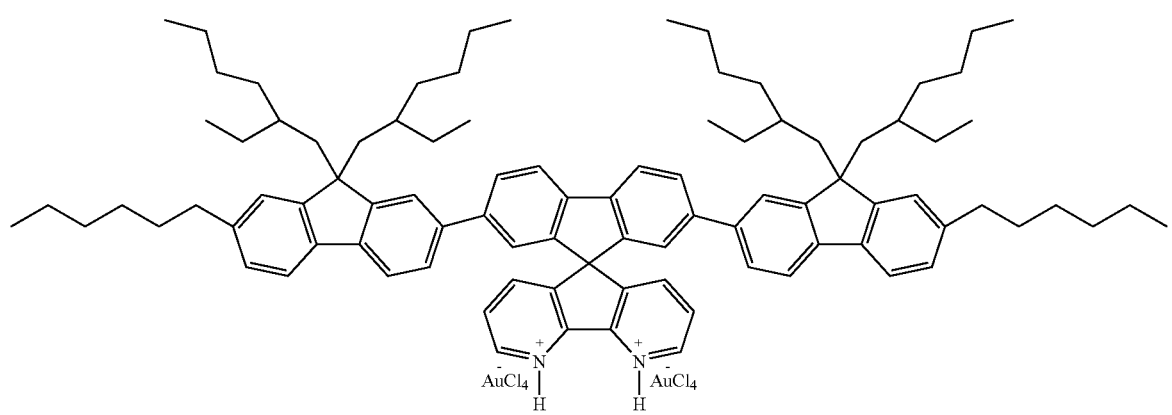

Formula (6)

However, the nitrogen-containing heteroaromatic ligand-transition metal complex may not be limited to the above formulas. In the above formulas, the linear or branched alkyl group, which is a substitution group, may include a methyl group, an ethyl group, a propyl group, an iso-butyl group, a sec-butyl group, a tert-butyl group, a pentyl group, an iso-amyl group and/or a hexyl group. One or more hydrogen atoms included in the alkyl group may be substituted with an alkyl group of about 1 to about 10 carbon atoms, a halogen atom, a hydroxyl group, a nitro group, an amino group, a cyano group, an alkoxy group, an amidino group, a hydrazine group and/or a carboxyl group.

In the hetero alkyl group, one or more carbon atoms, e.g., about 1 to about 5 carbon atoms, of a main chain of the alkyl group may be substituted with hetero atoms, e.g., oxygen (O), sulfur(S), nitrogen (N) and/or phosphorus (P). The aryl group may be a carbocycle aromatic system including one or more aromatic rings, and the rings may be attached or fused together using a pendent method. For example, the aryl group may include aromatic groups, e.g., a phenyl group, a naphthyl group and/or a tetrahydronaphthyl group. One or more hydrogen atoms in the aryl group may be substituted with the same substitution group as in the alkyl group.

The hetero aryl group may be a carbocycle aromatic system of about 5 to about 30 ring atoms, which may include one, two or three hetero atoms selected from among oxygen (O), sulfur (S), nitrogen (N) and phosphorus (P), and in which residual ring atoms are carbons (C). The rings may be attached or fused together using a pendent method. Further, one or more hydrogen atoms in the hetero aryl group may be substituted with the same substitution group as in the alkyl group.

The alkoxy group is a radical-O-alkyl, in which the alkyl is defined as above. For example, the alkoxy group may include a methoxy group, an ethoxy group, a propoxy group, an iso-butyloxy group, a sec-butyloxy group, a pentyloxy group, an iso-amyloxy group and/or a hexyloxy group. One or more hydrogen atoms in the alkoxy group may be substituted with the same substitution group as in the alkyl group.

The hetero alkoxy group may be essentially an alkoxy group, except that one or more hetero atoms, e.g., oxygen (O), sulfur (S) or nitrogen (N), may be present in an alkyl chain. Examples thereof may be $CH_3CH_2OCH_2CH_2O—$, $C_4H_9OCH_2CH_2OCH_2CH_2O—$ and/or $CH_3O(CH_2CH_2O)_n$H.

In the arylalkyl group, some of the hydrogen atoms in the aryl group as defined above may be substituted with lower alkyl groups, for example, radicals e.g., methyl, ethyl and/or propyl. Examples thereof may be a benzyl group and/or a phenylethyl group. One or more hydrogen atoms in the arylalkyl group may be substituted with the same substitution group as in the alkyl group.

In the hetero arylalkyl group, some of the hydrogen atoms therein may be substituted with lower alkyl groups. The hetero aryl group in the hetero arylalkyl group may be as defined above. One or more hydrogen atoms in the hetero arylalkyl group may be substituted with the same substitution group as in the alkyl group.

The aryloxy group may be a radical-O-aryl group, in which the aryl may be as defined above. For example, the aryloxy group may include a phenoxy group, a naphthoxy group, an anthracenyl oxy group, a phenanthrenyl oxy group, a fluorenyl oxy group and/or an indenyl oxy group. One or more hydrogen atoms in the aryloxy group may be substituted with the same substitution group as in the alkyl group.

The hetero aryloxy group may be a radical-O-heteroaryl group, in which the heteroaryl is as defined above. For example, the hetero aryloxy group may include a benzyloxy group and/or a phenylethyloxy group. One or more hydrogen atoms in the hetero aryloxy group may be substituted with the same substitution group as in the alkyl group.

The cycloalkyl group may be a monovalent monocyclic system of about 5 to about 30 carbon atoms. One or more hydrogen atoms in the cycloalkyl group may be substituted with the same substitution group as in the alkyl group.

The hetero cycloalkyl group may be a monovalent monocyclic system of about 5 to about 30 ring atoms, which may include one, two or three hetero atoms selected from among oxygen (O), sulfur (S), nitrogen (N) and phosphorus (P), and in which residual ring atoms are carbons (C). One or more hydrogen atoms in the hetero cycloalkyl group may be substituted with the same substitution group as in the alkyl group.

The alkylester group may be a functional group bonded with an alkyl group and an ester group. The alkyl group may be defined as above. The hetero alkylester group may be a functional group bonded with a hetero alkyl group and an ester group. The hetero alkyl group may be defined as above.

The aryl ester group may be a functional group bonded with an aryl group and an ester group. The aryl group may be defined as above. The hetero aryl ester group may be a functional group bonded with a hetero aryl group and an ester group. The hetero aryl group may be defined as above. The amino group may be $—NH_2$, $—NH(R)$ or $—N(R')(R'')$. Each of R' and R'' may be independently an alkyl group of about 1 to about 10 carbon atoms.

A nitrogen-containing heteroaromatic ligand-transition metal complex, represented by the above Formula (1), may be prepared by mixing a solution, in which a compound containing a nitrogen atom having an unshared electron pair in a ring thereof may be dissolved in a solvent, with a solution, in which a metal salt may be dissolved in a solvent, at about room temperature, or at a temperature of about 50° C. or less.

In a process of preparing a compound of example embodiments, a compound suitable for use as a metal salt may include gold chloride, platinum chloride, palladium chloride, copper chloride and/or palladium nitrate, but may not be limited thereto. The metal salt may be a metal halide, e.g., a metal chloride.

As a solvent for preparing each of the nitrogen-containing heteroaromatic ligand solution and metal salt solution, a general organic solvent, water, or a mixture thereof may be used. For example, organic solvents including alcohols, e.g., ethanol, ethers, chlorine-based alkanes, aromatics and glycols, water, mixed organic solvents, mixtures of one or more organic solvents and water may be used as the solvent, but may not be limited thereto. For example, those skilled in the art may use one or more suitable solvents selected from among the above solvents depending on the kind of the nitrogen-containing heteroaromatic ligand material, the kind of metal salt, and the intended use thereof.

The solvents for preparing the nitrogen-containing heteroaromatic ligand solution and the metal salt oxidizer solution may be the same as each other, or may be different from each other. The solvents may be the same as or similar to each other in the aspect of uniformity and ease of application.

When the nitrogen-containing heteroaromatic ligand solution is mixed with the oxidizer solution, a heteroaromatic ligand material may form a complex with metal ions in the oxidizer, so that the heteroaromatic ligand material may be oxidized. The oxidized heteroaromatic ligand material may be formed using a commonly known method.

Those skilled in the art may suitably select and determine a solvent having an increased solubility as the organic solvent depending on the structure and kind of specific compounds and metal salts. For example, the organic solvent may be any one selected from among alcohols, including methylalcohol, ethylalcohol, n-propylalcohol, iso-propylalcohol, n-butylalcohol, sec-butylalcohol, t-butylalcohol, iso-butylalcohol and/or diacetone alcohol, ketones including acetone, methylethylketone and/or methylisobutylketone, glycols including ethyleneglycol, diethyleneglycol, triethyleneglycol, propyleneglycol, butyleneglycol, hexylene glycol, 1,3-propanediol, 1,4-butanediol, 1,2,4-butanetriol, 1,5-pentanediol, 1,2-hexanediol and/or 1,6-hexanediol, glycolethers including ethyleneglycol monomethyl ether and/or triethyleneglycol monoethyl ether, glycol ether acetates, including propylene glycol monomethyl ether acetate (PGMEA), acetates, including ethyl acetate, butoxyethoxy ethyl acetate, butyl carbitol acetate (BCA) and/or dihydroterpineol acetate (DHTA), terpineols, Trimethyl pentanediol monoisobutyrate (TEXANOL), dichloroethene (DCE), chlorobenzene, xylene, and N-methyl-2-pyrrolidone (NMP), or a mixture thereof, but may not be limited thereto.

The nitrogen-containing heteroaromatic ligand solution may be prepared such that the concentration thereof is in the range of about 0.001 mM to about 100 mM, and the metal salt solution may be prepared such that the concentration thereof is in the range of about 0.1 mM to about 30 mM. However, the nitrogen-containing heteroaromatic ligand solution and the metal salt solution are not limited thereto. When the nitrogen-containing heteroaromatic ligand solution is mixed with the metal salt solution, a heteroaromatic ligand material may form a complex with metal ions in the metal salt, so that the heteroaromatic ligand material may be oxidized.

Example embodiments provide a buffer layer including the complex. When the buffer layer including the complex according to example embodiments is applied to the surface of the electrodes of an electronic device, the injection and transport of electrical charges between electrodes and a semiconductor layer or an electrical charge transfer layer may be improved, thereby improving the electrical characteristics of an electronic device. Such a buffer layer according to example embodiments may be formed as a thin film through commonly known methods.

For example, a mixed solution of a solution, in which a compound containing a nitrogen atom having an unshared electron pair in a ring thereof is dissolved in an organic solvent to produce the complex, and a solution, in which a metal salt H[M(Y)m] is dissolved in an organic solvent, may be formed into a thin film through conventional coating and deposition methods. Therefore, the buffer layer may be formed as a thin film.

Methods of forming the buffer layer may include a spin coating method, a dip coating method, a roll coating method, a screen coating method, a spray coating method, a spin casting method, a flow coating method, a screen printing method, an ink jet method, a drop casting method, and a vacuum deposition method, but may not be limited thereto.

The added amounts of the compound and metal salt may be suitably selected and determined depending on the intended use and state thereof by those skilled in the art. The added amounts thereof may be about 0.01 to about 10 parts by weight, based on about 100 parts by weight of a solvent. Tests of the formation of thin films showed that when the concentration of the complex is above about 10 wt %, because the concentration thereof may be relatively high, forming a uniform thin film may be relatively difficult. The buffer layer, which is formed through this process, may have a thickness of about 0.1 nm~about 100 nm, but may not be limited thereto. The thickness of the buffer layer may be suitably adjusted depending on the use and state thereof by those skilled in the art.

Example embodiments provide an electronic device including the buffer layer. Example embodiments provide an electronic device in which the buffer layer is formed on the surface of electrodes. When a buffer layer, according to example embodiments, is layered on the surface of electrodes, the contact resistance between the electrodes and a semiconductor layer may be reduced, so that the injection of electrons and holes, which are carriers, and the transportation of electrical charges between the layers may be accelerated. Accordingly, an electronic device including the buffer layer may exhibit improved electrical characteristics.

In example embodiments, the term "electronic device" refers to an electronic part featuring the conduction of electrons through a solid. The electronic devices, which may be used in example embodiments, may include an Organic Thin Film Transistors (OTFTs), Organic light emitting diodes (OLEDs), solar cells and/or organic photovoltaic devices, but may not be limited thereto.

For example, when applying the buffer layer, according to example embodiments, to an organic thin film transistor, the organic thin film transistor may include a substrate, a gate electrode, a gate insulation layer, a source electrode, drain electrode, a buffer layer, and an organic semiconductor layer. The buffer layer may include a nitrogen-containing heteroaromatic ligand-transition metal compound, represented by the following Formula (1), and may be formed on the gate electrode or the source/drain electrode.

$$[R_1-X-R_2].[M(Y)_m]^- \quad \text{Formula (1)}$$

wherein,

X is a substituted or unsubstituted nitrogen-containing heteroaromatic organic group of about 2 to about 30 carbon atoms, each of $R_1$ and $R_2$ is independently selected from the group consisting of a substituted or unsubstituted alkyl group of about 1 to about 30 carbon atoms; a substituted or unsubstituted hetero alkyl group of about 1 to about 30 carbon atoms; a substituted or unsubstituted alkoxy group of about 1 to about 30 carbon atoms; a substituted or unsubstituted hetero alkoxy group of about 1 to about 30 carbon atoms; a substituted or unsubstituted aryl group of about 6 to about 30 carbon atoms; a substituted or unsubstituted arylalkyl group of about 6 to about 30 carbon atoms; a substituted or unsubstituted aryloxy group of about 6 to about 30 carbon atoms; a substituted or unsubstituted hetero aryl group of about 2 to about 30 carbon atoms; a substituted or unsubstituted hetero arylalkyl group of about 2 to about 30 carbon atoms; a substituted or unsubstituted hetero aryloxy group of about 2 to about 30 carbon atoms; a substituted or unsubstituted cycloalkyl group of about 5 to about 20 carbon atoms; a hetero substituted or unsubstituted cycloalkyl group of about 2 to about 30 carbon atoms; a substituted or unsubstituted alkylester group of about 1 to about 30 carbon atoms; a substituted or unsubstituted hetero alkylester group of about 1 to about 30 carbon atoms; a substituted or unsubstituted aryl ester group of about 6 to about 30 carbon atoms; and a substituted or unsubstituted hetero aryl ester group of about 2 to about 30 carbon atoms, M is a transition metal atom selected from the group consisting of gold (Au), copper (Cu), palladium (Pd) and platinum (Pt), Y is selected from the group consisting of a halide, a hydroxyl group, and an acetate functional group (OAc), and m is an integer of about 3 to about 4.

In the above Formula (1), X may be selected from the group consisting of the heteroaromatic organic groups represented by the following Formula (2):

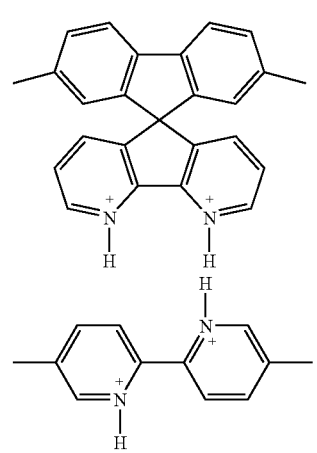

Formula (2)

-continued

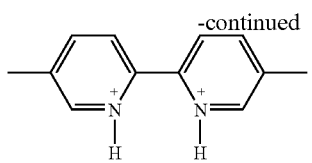

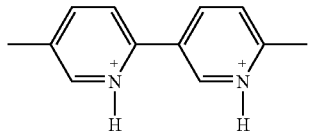

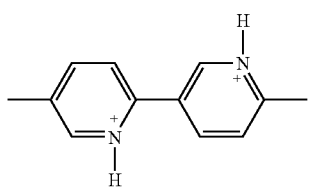

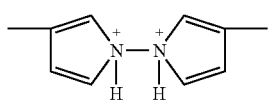

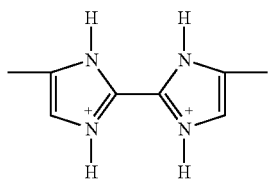

-continued

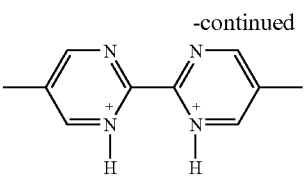

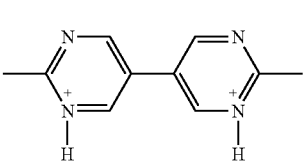

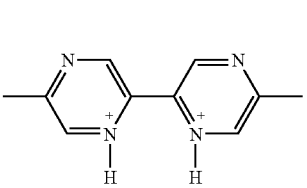

Further, in the above Formula (1), each of $R_1$ and $R_2$ may be independently a substituted or unsubstituted aryl group of about 6 to about 30 carbon atoms, or a substituted or unsubstituted hetero aryl group of about 2 to about 30 carbon atoms. A substitution group, with which the aryl group or hetero aryl group is substituted, may be one or more selected from the group consisting of a linear or branched alkyl group of about 1 to about 10 carbon atoms, a perfluoroalkyl group, a halogen atom, a hydroxy group, a nitro group, an amino group, a cyano group, an alkoxy group, an amidino group and a carboxyl group.

For example, the nitrogen-containing heteroaromatic ligand-transition metal complex may be represented by the following Formula (3):

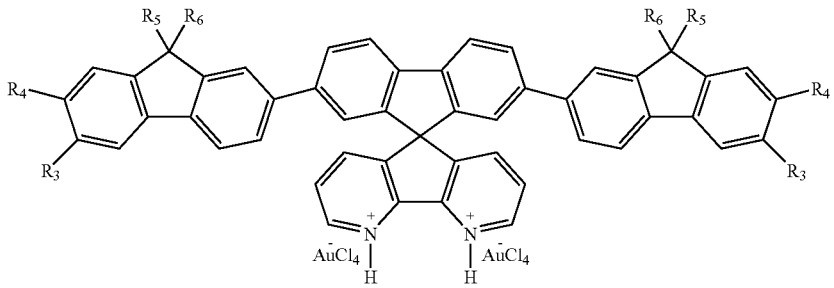

Formula (3)

wherein each of $R_3$ to $R_6$ may be independently selected from the group consisting of a linear or branched alkyl group of about 1 to about 10 carbon atoms, a perfluoroalkyl group, a hydrogen atom, a halogen atom, a hydroxy group, a nitro group, an amino group, a cyano group, an alkoxy group, an amidino group and a carboxyl group. At least one R may be a linear or branched alkyl group of about 1 to about 10 carbon atoms and/or a perfluoroalkyl group.

For example, the nitrogen-containing heteroaromatic ligand-transition metal complex may be represented by the following Formulas (4) to (6):

Formula (4)

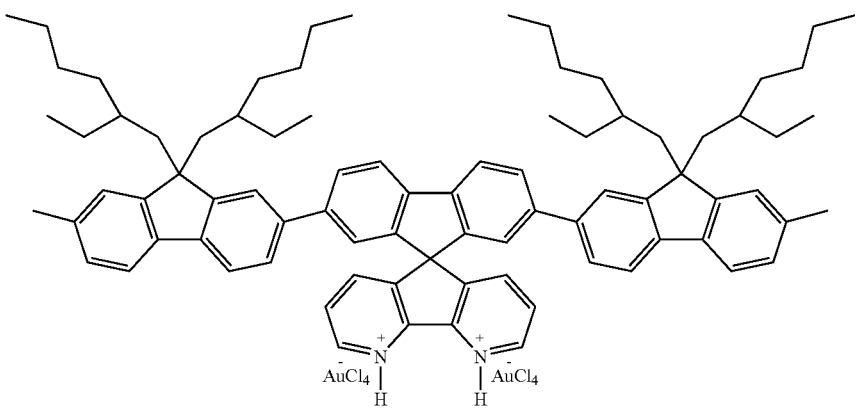

Formula (5)

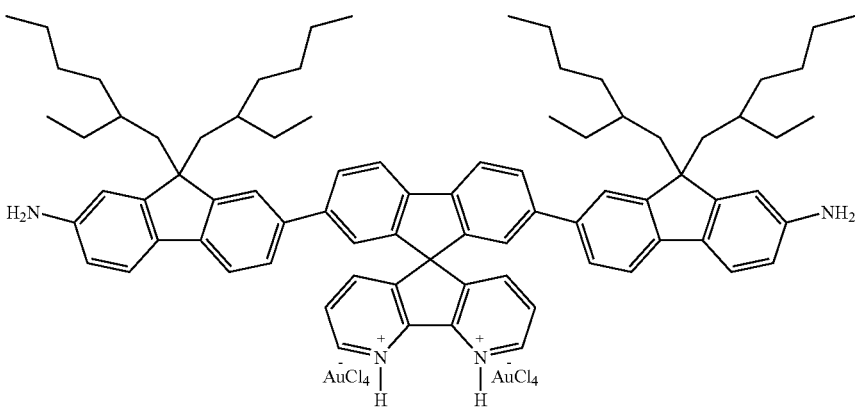

Formula (6)

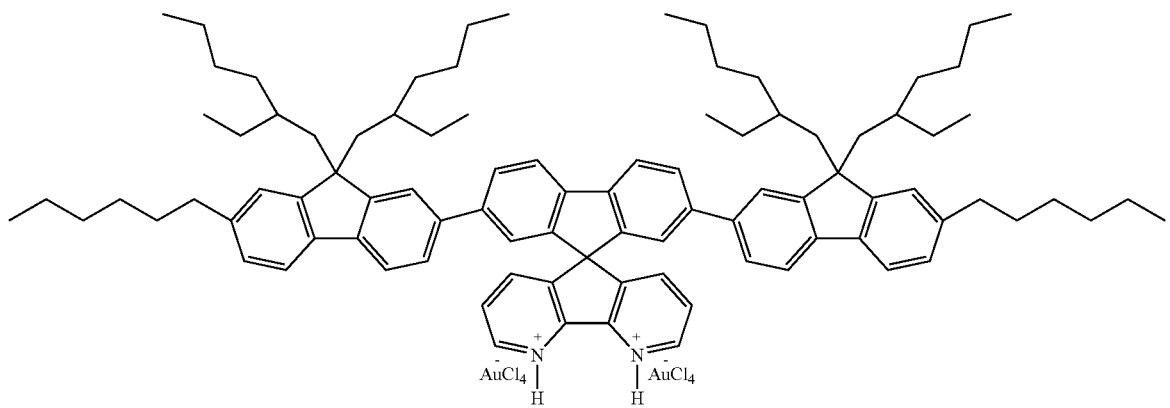

However, the nitrogen-containing heteroaromatic ligand-transition metal complex may not be limited to the above formulas. The organic thin film transistor may have other structures. The organic thin film transistor may have a structure that is modified within the scope of example embodiments. For example, as illustrated in FIG. 1, the OTFT 100 of example embodiments may have a top gate structure where source/drain electrodes 4,5, a buffer layer 6 on the surface of the source/drain electrodes 4,5, an organic semiconductor layer 7 between the source/drain electrodes 4,5, a gate insulation layer 3, and a gate electrode 2 are formed on a substrate 1.

Figure 2:
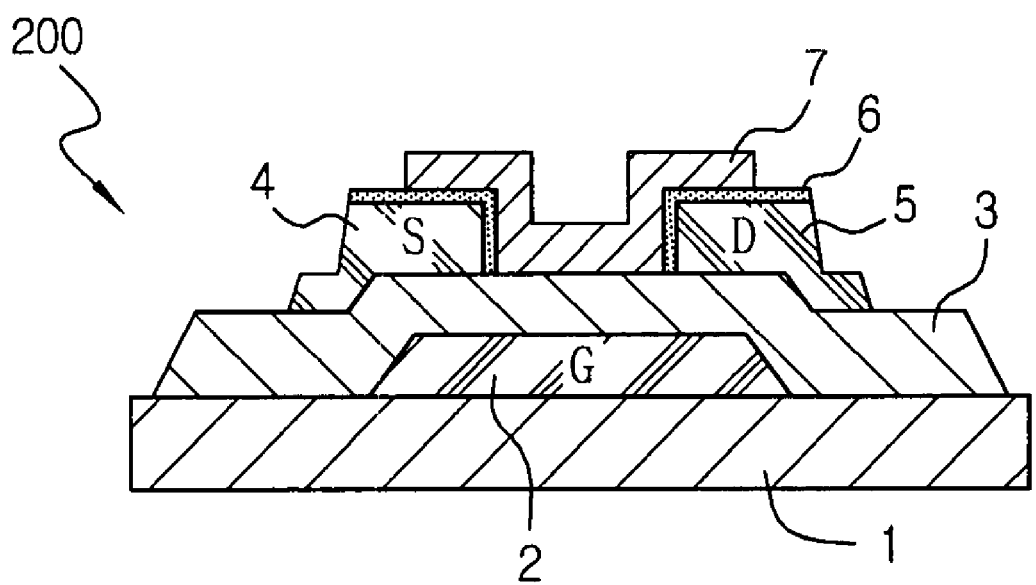

Also, as illustrated in FIG. 2, the OTFT 200 of example embodiments may have a bottom gate structure where a gate electrode 2, a gate insulation layer 3, source/drain electrodes 4,5, a buffer layer 6 on the surface of the source/drain electrodes 4,5, and an organic semiconductor layer 7 on the gate insulation film 3 and the source/drain electrodes 4,5, may be formed on a substrate 1. Further, in the electronic device according to example embodiments, constituents other than the buffer layer may be formed using materials commonly used in the technical field of example embodiments and formation methods thereof.

For example, in the case of an organic thin film transistor, glass, silicon and/or plastic may be used as the substrate. Further, metals, conductive polymers or metal oxides, which are commonly used, may be used as the gate electrode, source electrode or drain electrode. For example, the metals, conductive polymers or metal oxides may include gold (Au), silver (Ag), aluminum (Al), nickel (Ni), molybdenum (Mo), tungsten (W), indium-tin oxide (ITO), polythiophene, polyaniline, polyacetylene, polypyrrole, polyphenylene vinylene, a polyethylenedioxythiophene (EDOT)/polystyrene sulfonate (PSS) mixture and/or Indium-zinc oxide (IZO), but may not be limited thereto.

Further, organic materials, e.g., polyolefin, polyvinyl, polyacrylate, polystyrene, polyurethane, polyimide, polyvinylphenol and derivatives thereof, and inorganic materials, e.g., $SiN_x$ ($0<x<4$), $SiO_2$ and $Al_2O_3$, may be used as the gate insulation layer. Further, pentacene, tetracene, copper phthalocyanine, polythiophene, polyaniline, polyacetylene, polypyrrole, polyphenylene vinylene and derivatives thereof may be used as the organic semiconductor layer. However, the organic materials and inorganic materials may not be limited thereto.

When applying the buffer layer, according to example embodiments, to an organic light emitting diode, the organic light emitting diode may include a substrate, an anode, a buffer layer, a light emitting layer (EML), an electron transport layer (ETL), and a cathode. Constituents other than the buffer layer may be formed using materials commonly used in the technical field of example embodiments and formation methods thereof.

Hereinafter, example embodiments will be described in detail with reference to Examples. These Examples are set forth to illustrate example embodiments, but should not be construed as the limit of example embodiments.

Preparation Example 1

Synthesis of Flu-SPNB-Flu-Au 1-1: Synthesis of 9,9-bis(2-ethylhexyl)-9H-fluorene-2-ylbromic acid (bis(2-ethylhexyl)-9H-fluorene-2-ylbromoic acid (BFB)

2-bromo-9H-fluorene (about 5 g, about 20.4 mmol) and potassium t-butoxide (t-BuOK) (about 5.7 g, about 50 mmol) were dissolved in dimethylformamide (DMF), and then 2-ethylhexyl bromide (about 8 ml, about 44.9 mmol) was added thereto. Subsequently, the resultant was reacted at a temperature of about 40° C. for about 12 hours, and was then extracted using ethyl ether and distilled water. The unreacted 2-ethylhexyl bromide was removed through vacuum distillation. As a result, about 8.5 g (about 88%) BF-EH, represented by the following Formula (7), was obtained through column chromatography, in which petroleum ether was used as a developer.

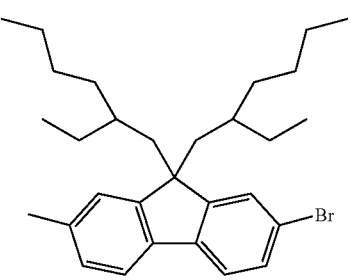

Formula (7)

The BF-EH (about 5 g, about 10.6 mmol) was dissolved in tetrahydrofuran (THF), and then about 5 ml n-BuLi (about 2.5M in hexane) was slowly added thereto at a temperature of about −78° C. for about 30 minutes. Subsequently, the resultant was stirred at a temperature of about −78° C. for about 1 hour, and then triisopropyl borate (about 2.97 mL, about 12.9 mmol) was added thereto. The resultant was reacted at about room temperature for about 12 hours, and was then extracted using ethyl ether and distilled water. As a result, about 3.2 g (about 69%) BFB, described in the heading, was obtained through column chromatography, in which petroleum ether/ethyl acetate was used as a developer.

1-2: Synthesis of Flu-SPNB-Flu

BFB (about 0.45 g, about 1.03 mmol) and SPNB (about 0.2 g, about 0.42 mmol), represented by the following Formula (8), were dissolved in about 30 mL toluene, and $Pd(PPh_3)_4$ (about 20 mg) and about 2.0 M $Na_2CO_3$ (about 4.2 mmol) were added thereto, and then the resultant was stirred at a temperature of about 9° C. for about 24 hours to obtain a reaction mixture. Subsequently, the obtained reaction mixture was cooled, extracted using petroleum ether, and dried using $MgSO_4$, thereby removing the solvent therefrom. The material remaining after the above processes was refined through column chromatography, in which an about 4:1 mixture of petroleum ether/ethyl acetate is used as the developer. As a result, about 0.3 g (about 64%) Flu-SPNB-Flu, represented by the following Formula (9), was obtained in the form of a white solid.

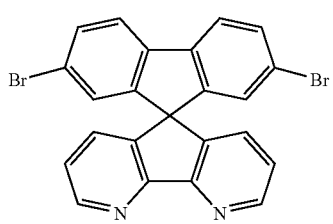

Formula (8)

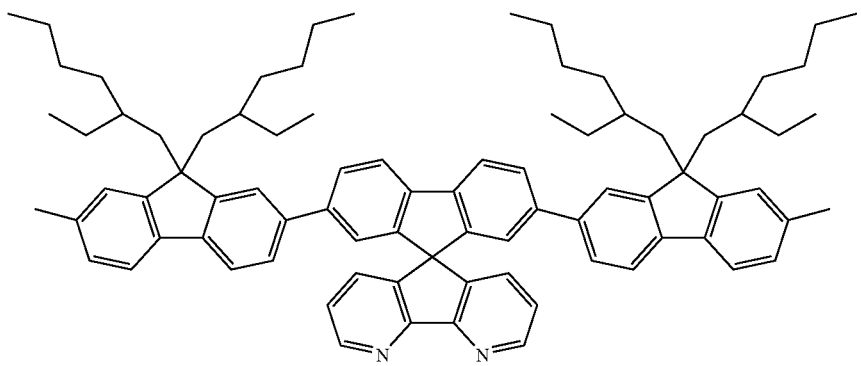

Formula (9)

1-3: Preparation of Flu-SPNB-Flu-Au Solution

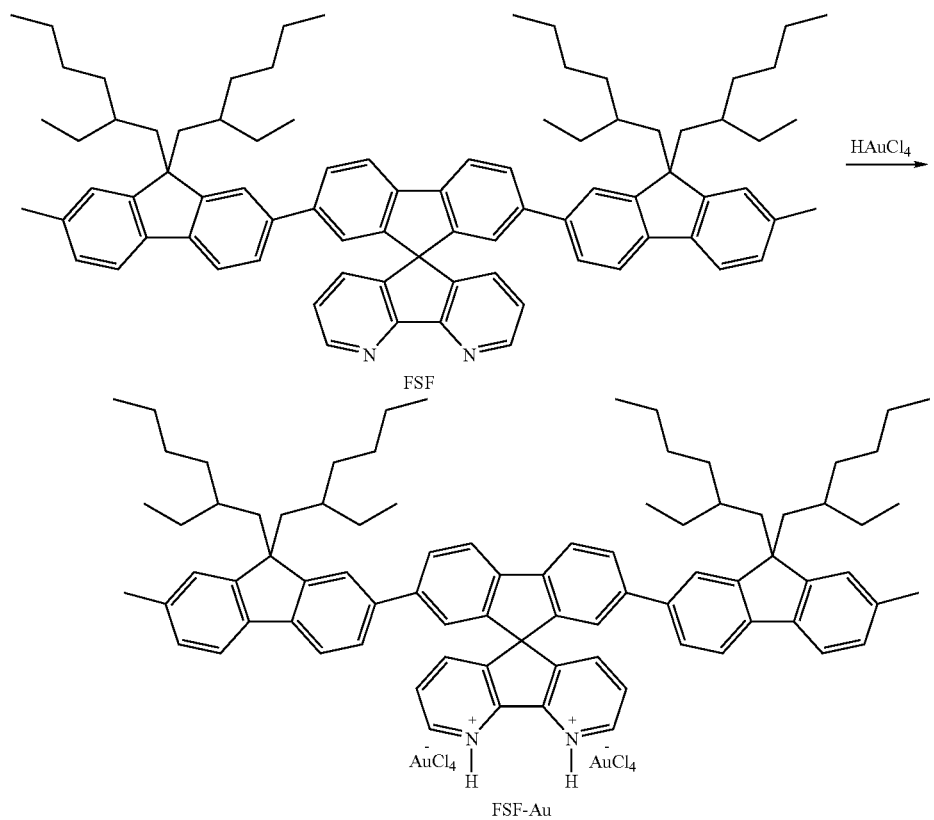

A solution (about 1 mM), in which about 10 mg Flu-SPNB-Flu may be dissolved in about 10 ml chlorobenzene, was mixed with a solution (about 0.1 mM), in which about 0.2 mg HAuCl$_4$ (oxidant) was dissolved in about 10 ml of chlorobenzene at a temperature of about 5° C. As a result, a Flu-SPNB-Flu-Au solution was prepared.

Preparation Example 2

A Flu-SPNB-Flu-Au solution was prepared using the same method as in Preparation Example 1, except that a solution (about 1 mM) in which about 2 mg HAuCl$_4$ (oxidant) was dissolved in about 10 ml chlorobenzene was used.

Preparation Example 3

A Flu-SPNB-Flu-Au solution was prepared using the same method as in Preparation Example 1 except that a solution (about 10 mM) in which about 20 mg HAuCl$_4$ (oxidant) was dissolved in about 10 ml chlorobenzene was used.

Preparation Example 4

Figure 3:
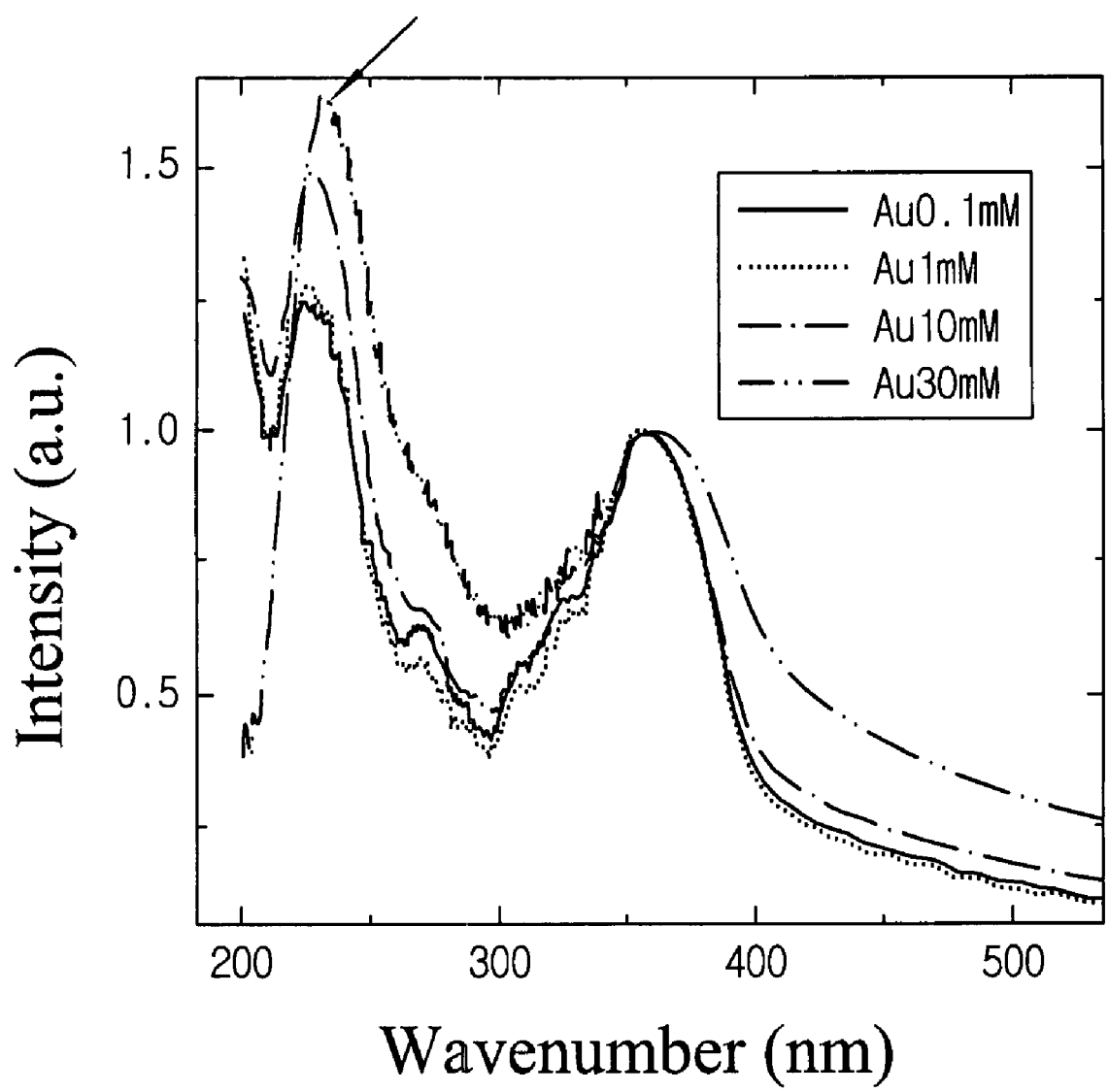

A Flu-SPNB-Flu-Au solution was prepared using the same method as in Preparation Example 1 except that a solution (about 30 mM) in which about 200 mg HAuCl$_4$ (oxidant) was dissolved in about 10 ml chlorobenzene was used.
FIG. 3 shows a UV-visible spectrum graph of Flu-SPNB-Flu-Au synthesized in Preparation Examples 1 to 4. As shown in FIG. 3, ligand-to-metal charge transport bands were formed.

Example 1

Figure 4:
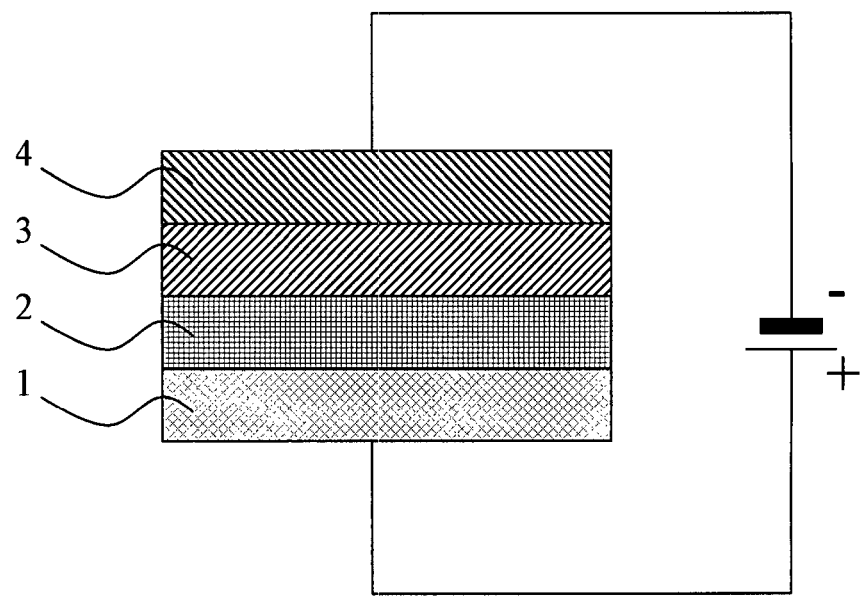

Manufacture of Devices Similar to Diodes and Comprising a Flu-SPNB-Flu-Au Buffer Layer As shown in FIG. 4, a mixed solution of a Flu-SPNB-Flu-Au complex, synthesized in Preparation Example 1, was applied on a glass substrate coated with indium-tin oxide (ITO), which is a patterned lower electrode 1, using a spin coating method at a rotation speed of about 1000 rpm, thereby forming a buffer layer 2 having a thickness of about 10 nm. Subsequently, an organic semiconductor layer 3 having a thickness of about 70 nm was formed by thermal-depositing pentacene at a pressure of about $10^{-6}$ Torr, and an upper electrode 4 was formed by thermal depositing Au to a thickness of about 70 nm, thereby manufacturing a test device having a structure similar to a diode.

Comparative Example 1

Figure 5:
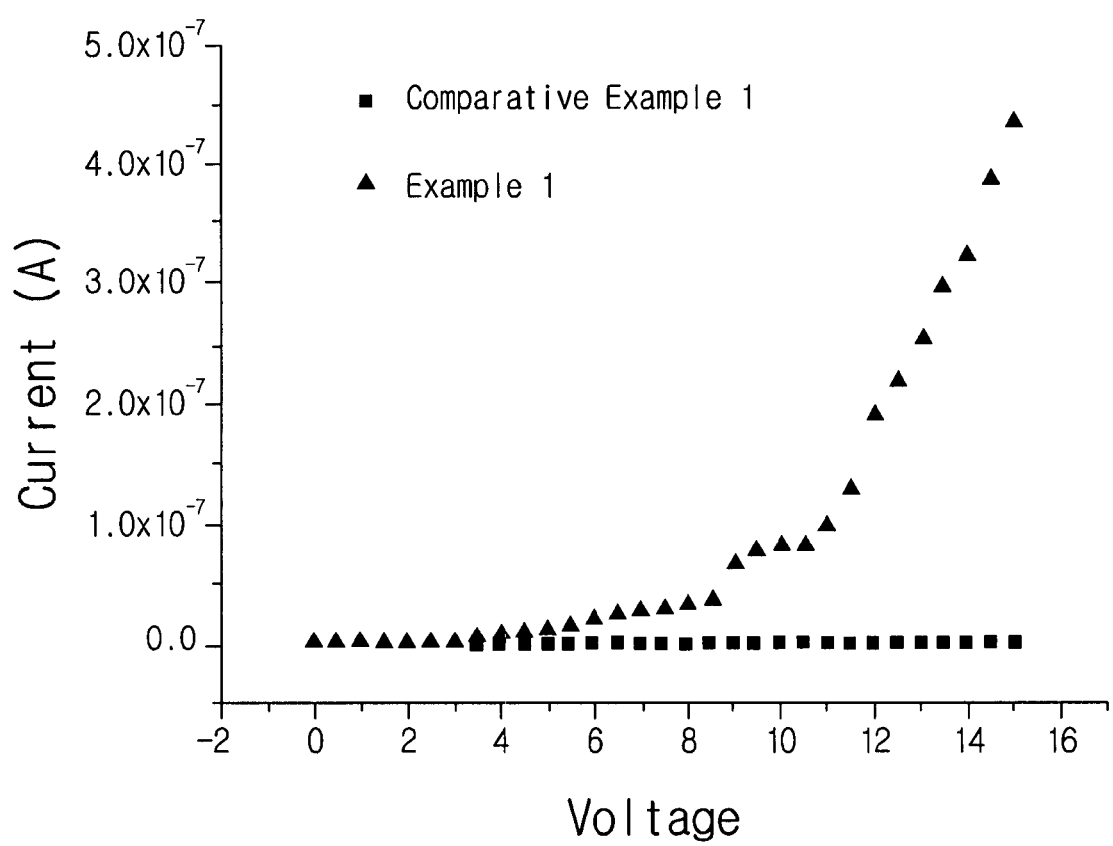

A test device having a structure similar to a diode was manufactured using the same method as in Example 1, except that no buffer layer was formed.
FIG. 5 shows the current-voltage characteristic of devices similar to the diode in Example 1 and Comparative Example 1. The variation of current was evaluated while the (+) electrode was connected to indium-tin oxide (ITO), the (−) electrode was connected to Au, and the voltage was increased, in order to determine the effect of injecting holes into a channel layer in the ITO which may be used in a backplane for a large area display.

Referring to FIG. 5, in the case of Example 1, in which the device may include a buffer layer containing the complex of example embodiments, when the voltage was about 14 V, the current was about $4.0 \times 10^{-7}$ A. Therefore, the current in Example 1 was increased, compared to that in Comparative Example 1, in which the device may not include a buffer layer. Accordingly, the adhesiveness between ITO and pentacene was improved through the buffer layer containing the complex, and that the injection and transport of electrical charges was improved by matching the energy level of the buffer layer with that of the pentacene.

Accordingly, example embodiments provide a nitrogen-containing heteroaromatic ligand-transition metal complex, a buffer layer including the complex, which may improve the injection and transport of electrical charges, and an electronic device including the buffer layer, in which the injection of electrons or holes and the transport of charges between layers may be accelerated, thereby exhibiting improved electrical characteristics.

As described above, although example embodiments have been disclosed for illustrative purposes, those skilled in the art will appreciate that various modifications, additions and substitutions are possible, without departing from the scope and spirit of the accompanying claims.

What is claimed is:

1. A nitrogen-containing heteroaromatic ligand-transition metal complex, represented by the following Formula (1):

$$[R_1-X-R_2] \cdot [M(Y)_m]^- \qquad \text{Formula (1)}$$

wherein,

X is represented by the following Formula (2):

Formula (2)

each of $R_1$ and $R_2$ is independently selected from the group consisting of a substituted or unsubstituted alkyl group of about 1 to about 30 carbon atoms; a substituted or unsubstituted hetero alkyl group of about 1 to about 30 carbon atoms; a substituted or unsubstituted alkoxy group of about 1 to about 30 carbon atoms; a substituted or unsubstituted hetero alkoxy group of about 1 to about 30 carbon atoms; a substituted or unsubstituted aryl group of about 6 to about 30 carbon atoms; a substituted or unsubstituted arylalkyl group of about 6 to about 30 carbon atoms; a substituted or unsubstituted aryloxy group of about 6 to about 30 carbon atoms; a substituted or unsubstituted hetero aryl group of about 2 to about 30 carbon atoms; a substituted or unsubstituted hetero arylalkyl group of about 2 to about 30 carbon atoms; a substituted or unsubstituted hetero aryloxy group of about 2 to about 30 carbon atoms; a substituted or unsubstituted cycloalkyl group of about 5 to about 20 carbon atoms; a hetero substituted or unsubstituted cycloalkyl group of about 2 to about 30 carbon atoms; a substituted or unsubstituted alkylester group of about 1 to about 30 carbon atoms; a substituted or unsubstituted hetero alkylester group of about 1 to about 30 carbon atoms; a substituted or unsubstituted aryl ester group of about 6 to about 30 carbon atoms; and a substituted or unsubstituted hetero aryl ester group of about 2 to about 30 carbon atoms, M is a transition metal atom selected from the group consisting of gold (Au), copper (Cu), palladium (Pd) and platinum (Pt), and the transition metal atom forms a complex with a nitrogen atom of the substituted or unsubstituted nitrogen-containing heteroaromatic organic group, Y is selected from the group consisting of a halide, a hydroxyl group, and an acetate functional group (OAc), and m is an integer of about 3 to about 4.

2. The complex according to claim 1, wherein each of the $R_1$ and $R_2$ is independently a substituted or unsubstituted aryl group of about 6 to about 30 carbon atoms, or a substituted or unsubstituted hetero aryl group of about 2 to about 30 carbon atoms.

3. The complex according to claim 2, wherein a substitution group, with which the aryl group or hetero aryl group is substituted, is one or more selected from the group consisting of a linear or branched alkyl group of about 1 to about 10 carbon atoms, a perfluoroalkyl group, a halogen atom, a hydroxy group, a nitro group, an amino group, a cyano group, an alkoxy group, an amidino group and a carboxyl group.

4. A buffer layer comprising the complex according to claim 1.

5. The buffer layer according to claim 4, wherein the buffer layer is formed as a thin film using a spin coating method, a dip coating method, a roll coating method, a screen coating method, a spray coating method, a spin casting method, a flow coating method, a screen printing method, an ink jet method, a drop casting method, or a vacuum deposition method.

6. The buffer layer according to claim 4, wherein a thickness of the buffer layer is in a range from about 0.1 nm to about 100 nm.

7. An organic thin film transistor, comprising:
a substrate;
a gate electrode;
a gate insulation layer;
a source electrode;
a drain electrode;
a buffer layer; and
an organic semiconductor layer,
wherein the buffer layer is the buffer layer of claim 4, and is formed on the source/drain electrode.

8. The organic thin film transistor according to claim 7, wherein each of the $R_1$ and $R_2$ is independently a substituted or unsubstituted aryl group of about 6 to about 30 carbon atoms, or a substituted or unsubstituted hetero aryl group of about 2 to about 30 carbon atoms.

9. The organic thin film transistor according to claim 8, wherein a substitution group, with which the aryl group or hetero aryl group is substituted, is one or more selected from the group consisting of a linear or branched alkyl group of about 1 to about 10 carbon atoms, a perfluoroalkyl group, a halogen atom, a hydroxy group, a nitro group, an amino group, a cyano group, an alkoxy group, an amidino group and a carboxyl group.

10. An electronic device comprising the buffer layer according to claim 4.

11. The electronic device according to claim 10, wherein the electronic device is an Organic Thin Film Transistor (OTFTs), an organic light emitting diode (OLEDs), solar cell and/or organic photovoltaic device.

* * * * *